(12) United States Patent
Jennings-Spring

(10) Patent No.: US 7,645,252 B2
(45) Date of Patent: Jan. 12, 2010

(54) BODY OR PLANT PART DRESSING

(76) Inventor: Barbara Brooke Jennings-Spring, 10844 N. Dogwood Trail, Jupiter, FL (US) 33478

(*) Notice: Subject to any disclaimer, the term of this patent is extended or adjusted under 35 U.S.C. 154(b) by 104 days.

(21) Appl. No.: 11/434,689

(22) Filed: May 16, 2006

(65) Prior Publication Data

US 2007/0270737 A1 Nov. 22, 2007

(51) Int. Cl.
*A61F 13/06* (2006.01)
*A61F 15/00* (2006.01)
*A61F 13/00* (2006.01)
*A61F 13/02* (2006.01)

(52) U.S. Cl. .................. 602/63; 604/304; 604/307; 604/308; 602/48; 602/58; 602/61; 602/901

(58) Field of Classification Search ................ 604/304, 604/307, 358, 385.01, 385.03, 385.04, 385.14, 604/387, 308, 174, 179–180, 312; 602/41, 602/53, 43, 54, 61, 62, 79, 901, 21, 22, 23, 602/30, 42, 52, 63, 64, 65, 66
See application file for complete search history.

(56) References Cited

U.S. PATENT DOCUMENTS

| | | | |
|---|---|---|---|
| 1,615,945 A | 2/1927 | James | |
| 2,226,546 A * | 12/1940 | Bower | 602/57 |
| 2,387,642 A | 10/1945 | Calhoun | |
| 2,401,714 A | 6/1946 | Weil | |
| 2,564,183 A | 8/1951 | Wilson | |
| 2,646,796 A | 7/1953 | Scholl | |
| 2,882,528 A | 4/1959 | Tassie | |
| 3,263,681 A | 8/1966 | Nechtow et al. | |
| 3,710,790 A | 1/1973 | Lemon | |
| 3,880,159 A | 4/1975 | Diamond | |
| 4,165,748 A * | 8/1979 | Johnson | 604/180 |
| 4,176,664 A | 12/1979 | Kalish | |
| 4,333,468 A * | 6/1982 | Geist | 604/180 |
| 4,423,722 A | 1/1984 | Dickman | |
| 4,523,586 A * | 6/1985 | Couri | 602/3 |
| 4,569,348 A * | 2/1986 | Hasslinger | 604/179 |
| 4,576,599 A | 3/1986 | Lipner | |
| 4,983,163 A | 1/1991 | Winans | |
| 5,074,315 A | 12/1991 | McCuiston | |
| 5,085,210 A | 2/1992 | Smith, III | |
| 5,158,556 A | 10/1992 | Starley | |
| 5,163,914 A * | 11/1992 | Abel | 604/180 |
| 5,163,943 A | 11/1992 | Mohiuddin et al. | |
| 5,183,460 A | 2/1993 | Scherz | |
| 5,209,718 A | 5/1993 | McDaniel | |
| 5,269,788 A | 12/1993 | Nelson, III | |
| 5,275,592 A | 1/1994 | Grizzaffi | |
| 5,439,466 A | 8/1995 | Kilejian | |
| 5,527,293 A * | 6/1996 | Zamierowski | 604/176 |
| 5,592,953 A | 1/1997 | Delao | |
| 5,618,302 A | 4/1997 | Martin | |
| 5,642,525 A | 7/1997 | Ketola | |
| 5,643,183 A * | 7/1997 | Hill | 602/3 |

(Continued)

*Primary Examiner*—Leslie Deak
*Assistant Examiner*—Adam Marcetich

(57) ABSTRACT

A dressing having a flexible sleeve shaped to accommodate a substantially cylindrical body or plant portion, the sleeve having a lining which is substantially non-adherent to the body or plant part being bandaged and having a peripheral securement means which attaches two peripheral portions to each other without those portions being circumferentially adhered to the sleeve portion.

17 Claims, 9 Drawing Sheets

U.S. PATENT DOCUMENTS

| | | | |
|---|---|---|---|
| 5,649,933 A | 7/1997 | Singh | |
| 5,674,189 A * | 10/1997 | McDowell et al. | 602/62 |
| 5,690,610 A | 11/1997 | Ito et al. | |
| 5,722,575 A * | 3/1998 | Smith | 224/217 |
| 5,741,511 A | 4/1998 | Lee et al. | |
| 5,769,808 A | 6/1998 | Matthijs et al. | |
| 5,797,401 A | 8/1998 | Knight | |
| 5,807,299 A | 9/1998 | McRoberts et al. | |
| 5,817,038 A | 10/1998 | Orange et al. | |
| 5,860,988 A | 1/1999 | Rawlings | |
| 5,914,125 A * | 6/1999 | Andrews et al. | 424/443 |
| 5,925,008 A | 7/1999 | Douglas | |
| 5,935,091 A * | 8/1999 | Friedman | 602/79 |
| 5,947,998 A | 9/1999 | Cartmell et al. | |
| 5,989,567 A | 11/1999 | Dolisi | |
| 6,051,249 A | 4/2000 | Samuelsen | |
| 6,068,607 A | 5/2000 | Palmer | |
| 6,290,653 B1 * | 9/2001 | Che et al. | 600/490 |
| 6,307,118 B1 | 10/2001 | Reich | |
| 6,309,344 B1 | 10/2001 | Werner | |
| 6,311,933 B1 * | 11/2001 | Starchevich | 248/65 |
| 6,323,386 B1 * | 11/2001 | Stapf et al. | 602/41 |
| 6,378,745 B1 * | 4/2002 | De Luccia | 224/218 |
| 6,441,265 B1 * | 8/2002 | Chan | 602/53 |
| 6,580,011 B1 | 6/2003 | Jennings-Spring | |
| 6,617,485 B2 * | 9/2003 | Herzberg | 602/41 |
| 2001/0001883 A1 | 5/2001 | Wanzenried | |
| 2001/0047144 A1 * | 11/2001 | Tillotson et al. | 602/41 |
| 2002/0095107 A1 | 7/2002 | Martin | |
| 2002/0153013 A1 * | 10/2002 | Single et al. | 128/885 |
| 2003/0093075 A1 | 5/2003 | Levinson | |
| 2003/0131411 A1 * | 7/2003 | Gibson | 5/482 |
| 2003/0139698 A1 * | 7/2003 | Hyson | 602/61 |
| 2004/0019308 A1 | 1/2004 | Chow | |
| 2004/0073152 A1 * | 4/2004 | Karason et al. | 602/41 |

* cited by examiner

BODY OR PLANT PART DRESSING

CROSS-REFERENCE TO RELATED APPLICATIONS

Not applicable.

STATEMENT REGARDING FEDERALLY SPONSORED RESEARCH OR DEVELOPMENT

Not Applicable

FIELD OF THE INVENTION

The invention relates to dressings for injured body or plant parts which parts are primarily cylindrical in shape over which the dressing is to be applied. In horticultural applications, it is particularly applicable to dressings applied to grafting cites and plant parts to which the dressing can be readily applied. In human and animal contexts, the invention is especially applicable to cylindrical body parts such as a finger, palm, wrist, arm, toes, toe, foot, ankle, leg, and the penis. It is also applicable to bandages applied around the ear, and in various arrangements around the head such as a bandana around a portion of the forehead, eyebrows, especially in the context of cosmetic or reconstructive surgery. In short, given the appropriate sized bandage of the invention, it is applicable to any wound or administration area where the bandage can be applied by slipping the body part needing to be bandaged into the bandage and the bandage can be adequately secured by closing the flaps as described below. The invention most particularly relates to the field of dressings for the recently circumcised or injured penis.

BACKGROUND OF THE INVENTION

Circumcision is commonly performed on newborn infants, but may also be performed on young children, adolescents, and sometimes adults. Prior art is discussed in detail in my U.S. Pat. No. 6,580,011, which is incorporated herein in its entirety by reference. In addition to the prior art discussed there, U.S. Pat. No. 5,935,091 relates to a hemostatic circumcision bandage. The shaft supporting portion includes attachment portions to hold a resilient pad in place. The resilient pad is used to facilitate hemostasis.

These prior art disclosures share a common failing. The bandages there are all secured by placing ends or strap-like portions around the circumference of the penis in such a way that either too much pressure or too little pressure is applied. If too much pressure is applied as the straps are wrapped too tightly, the bandage causes discomfort, and may even adversely affect the healing process. Bandages that have been applied too tightly cause discomfort, can cut off proper blood flow to the body portions distal to the bandage, and in the case of penile bandages, have been reported to cut off urine flow so that there is urinary retention with potential for increased risk of infection and in severe cases, bladder rupture. If the straps are not wrapped tightly enough, the bandage will be loose and can easily fall off the penis, leaving the wounded area unprotected. A loose bandage can also result in unacceptable abrasion of the wound area and potentially causing the wound to reopen. The "loose" bandage is particularly problematic in the case of infant circumcision as substantial movement and abrasion could occur in the act of diapering the child.

The present invention solves this problem by making it extremely easy for the applier to apply precisely the right amount of pressure to create not only a secure bandage, but a bandage that will promote hemostatic healing. Furthermore, the bandage can be removed without any interference with the healing body part.

OBJECTS OF THE INVENTION

It is therefore an object of the invention to provide a dressing for a substantially cylindrically shaped body part with a securement means allowing the dressing to be applied with the proper amount of pressure in order to promote hemostasis.

It is another object of the invention to provide a surgical dressing for a recently injured penis allowing for application with appropriate pressure to facilitate healing.

It is yet another object of the invention to provide a dressing for an animal or human substantially cylindrical body part or substantially cylindrical plant part that permits easy removal of the dressing without involving the bandaged part in the removal process.

It is still a further object of the invention to provide a surgical dressing for a recently circumcised penis with appropriate pressure applied so as to promote hemostasis.

Yet another object of the invention is to provide a surgical dressing which preserves hygienic conditions by providing an improved securement means.

Still another object of the invention is to provide a cosmetic tool for the application of cosmetics to fingernails and toenails while allowing the applier to move other digits in a hygienic manner and not disturb the application of the cosmetic to other nearby digits.

Still another object of the invention is to provide a dressing for the treatment of plant parts in a manner which allows for the application of the dressing with appropriate pressure and/or its removal without involvement of the plant part.

An even further object of the invention is to provide a medicated or pesticidal impregnated dressing which can be applied to a substantially cylindrically shaped plant part to create a pesticidal barrier without application of the same to the soil or foliage and allows for the expansion of the plant part as the plant grows.

A still further object of the invention is to provide a bandage suitable for at least one of (a) maintaining hemostasis; (b) topical administration of an agent, or (c) transdermal administration of an agent without the need for a skin-contacting-adhesive.

Another object of the invention is to provide a skin-contacting adhesiveless transdermal device for active agents that are poorly skin penetrating without the use of or with lesser amounts of skin penetration enhancers.

Even further objects of the invention will be apparent to those of ordinary skill in the art.

BRIEF SUMMARY OF THE INVENTION

These and other objects of the invention are surprisingly achieved by a dressing having a flexible sleeve shaped to accommodate a substantially cylindrical body or plant portion, the sleeve having a lining which is substantially non-adherent to the body or plant part being bandaged and having a peripheral securement means which attaches two peripheral portions to each other without those portions being circumferentially adhered to the sleeve portion.

BRIEF DESCRIPTION OF THE DRAWINGS

Embodiments that are presently preferred are shown in the drawings; however, the invention is not limited to the precise arrangements and instrumentalities shown, wherein:

FIG. 15A is an enlarged view of the sleeve portion of a present invention device into which the body or plant part is to be inserted, while

DETAILED DESCRIPTION OF THE INVENTION

The present invention (shown with respect to particular embodiments in FIGS. 1-20) is generally directed to a dressing having a flexible sleeve portion or tubular shaped portion shaped to accommodate a substantially cylindrical body or plant portion, the sleeve portion or tubular shaped portion having a lining which is substantially non-adherent to the body or plant part being bandaged and having a peripheral securement means which attaches two peripheral portions to each other without those portions being circumferentially adhered to the sleeve portion. FIGS. 1-5 show the various views of a device (1) of the invention in a closed position about a body part that has been inserted through sleeve opening 11, although only FIG. 1 (of FIGS. 1-5) shows the body part (dotted line). The remaining elements of these FIGS. 1-5 are described more specifically with respect to FIGS. 6-10 below.

Figure 1:
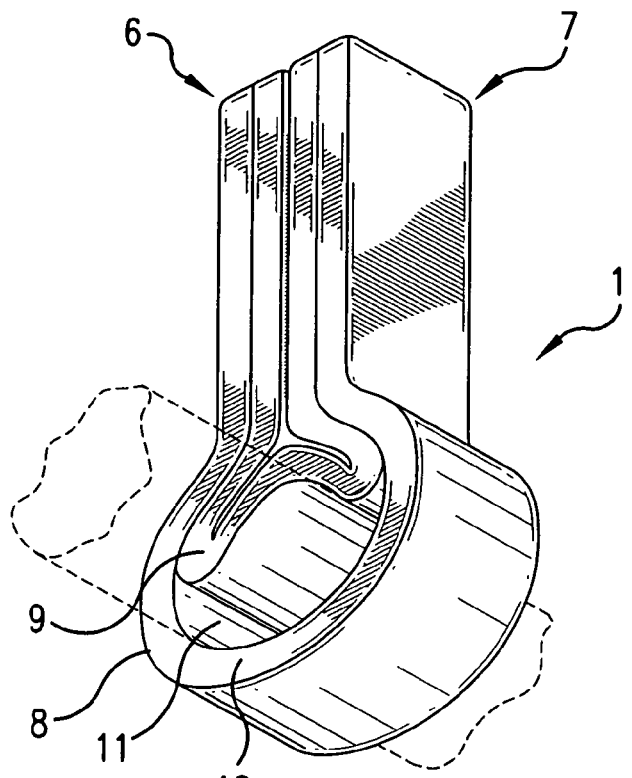
FIG. 1 is a perspective view of a device of the present invention secured around a body or plant part.
Figure 2:
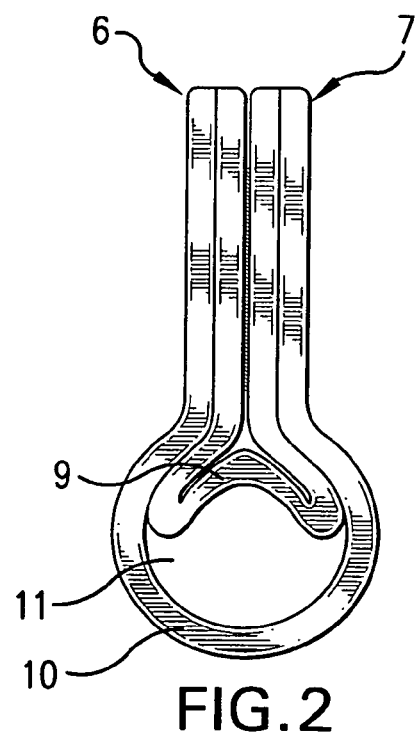
FIG. 2 is a front view of the device of FIG. 1 in the secured position (omitting the body part around which it is secured.
Figure 3:
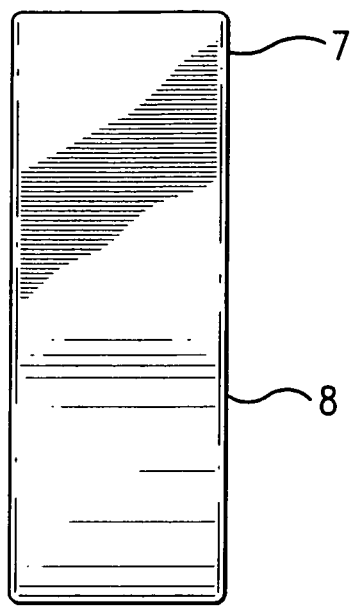
FIG. 3 is side view of the device of FIG. 1 in the secured position.
Figure 4:
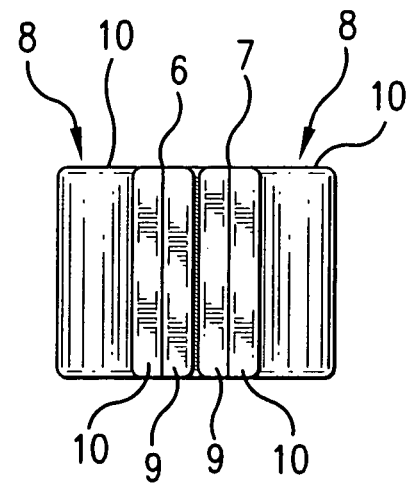
FIG. 4 is a top view of the device of FIG. 1 in the secured position.
Figure 5:
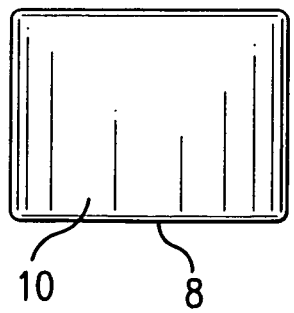
FIG. 5 is a bottom view of the device of FIG. 1 in the secured position.
Figure 6:
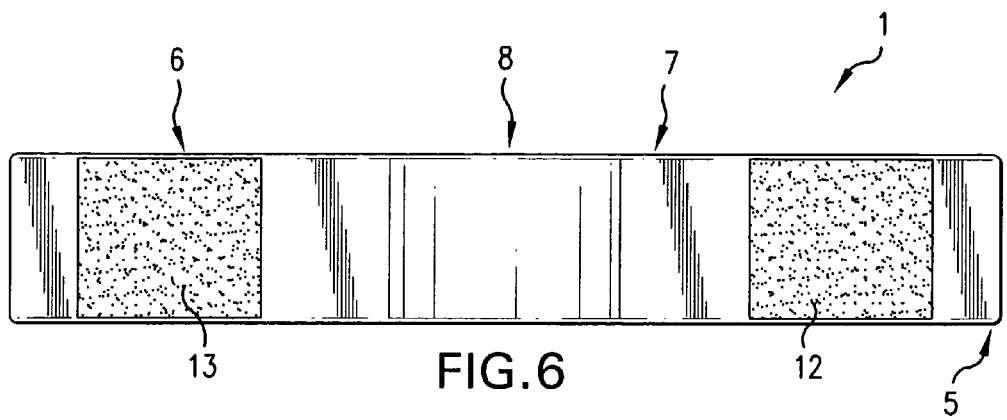
FIG. 6 is a top planar view of the device of FIG. 1 in pre-use unfolded position.
Figure 7:
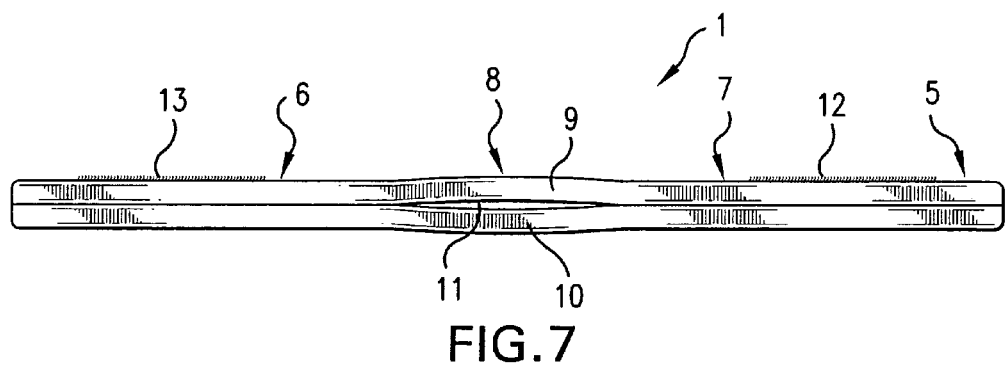
FIG. 7 is a front planar view of the device of FIG. 1 in pre-use unfolded position.
Figure 8:
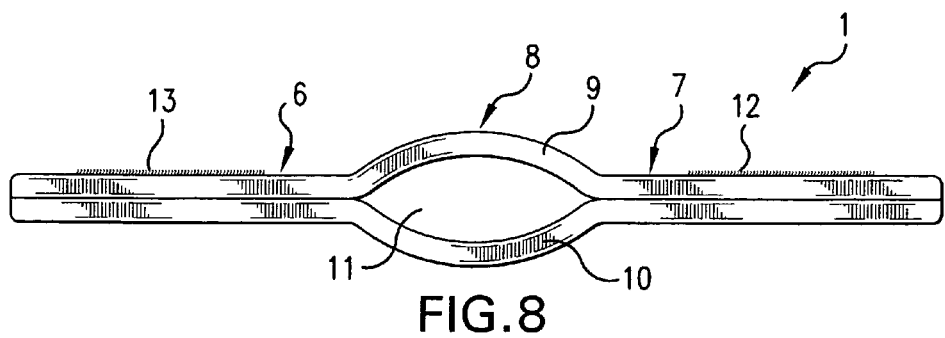
FIG. 8 is a front planar view of the device of FIG. 7 in pre-use unfolded position that has been opened for use.
Figure 9:
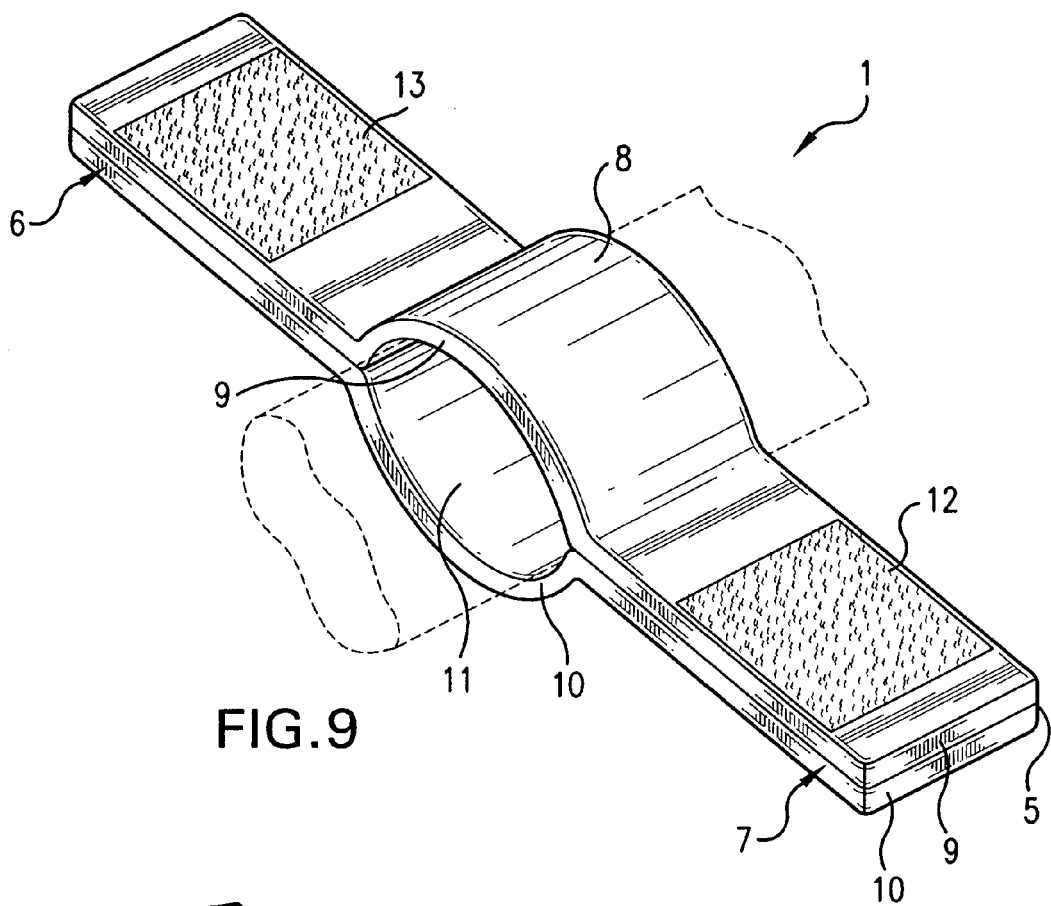
FIG. 9 is perspective view of the device of FIG. 8 showing placement on the body part being dressed prior to closure for securement.
Figure 10:
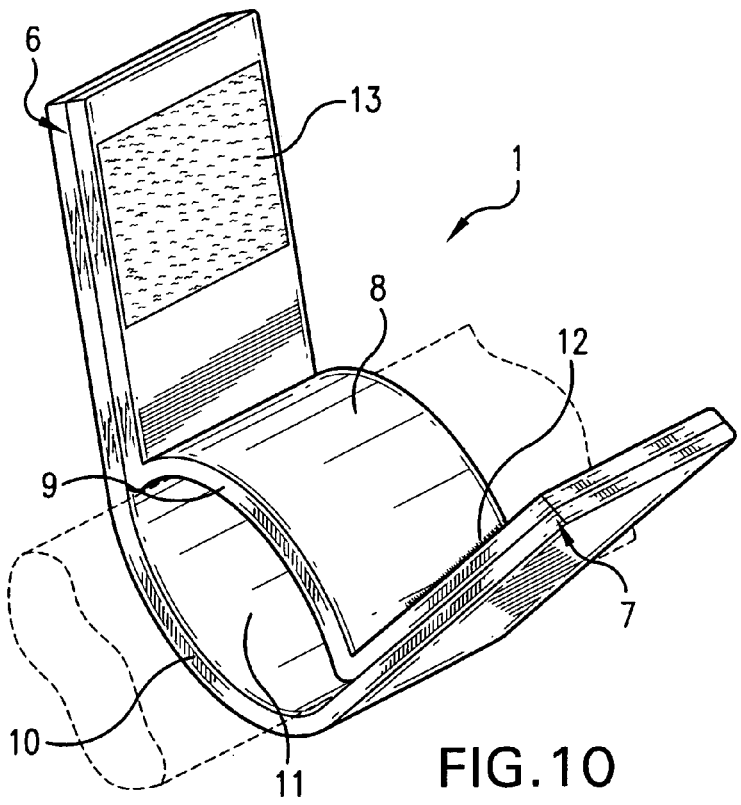
FIG. 10 is a perspective view of the device in FIG. 9 showing partial displacement of the peripheral flaps in the act of securing the device.

In FIGS. 6 and 7, the invention device 1 is shown in a flat, pre-use, unopened position and is shown as generally elongated member 5. Generally elongated member 5 is divided into left and right flaps 6 and 7 and a central portion 8. Generally elongated member 5 is bifurcated into a top portion 9 and a bottom portion 10, which are adhered to each other in the left and right flap portions 6 and 7, but not in central portion 8 so as to create between them sleeve opening 11 in central region 8. When flap portions 6 and 7 are displaced centrally inward, top portion 9 and bottom portion 10 can be displaced from one another such as shown in FIG. 8 to open sleeve 11 in anticipation of applying the device to an appropriate body or plant part. Securement means 12 and 13 are placed so that once the device is placed on the body or plant part, the peripheral ends of flaps 6 and 7 (distal from central portion 8) can be grasped and brought together so that securement means 12 and 13 are substantially mated to one another and result in securing the device in place without adhering to central portion 8. In the course of bringing flaps 6 and 7 together, the top portion 9 may fold into a position as shown more specifically in FIGS. 1 and 2. It should be noted that although the figures show the securement means across a substantial potion of the flaps 6 and 7, the area of flaps 6 and 7 having a securement means thereon can vary in both length and width as desired so long as the securement means, when moved to a closed position about a body part do not adhere to circumferential areas of the central portion 8, but only to securement means areas. An alternative embodiment has flaps 6 and 7 extending a minimum distance from central portion 8 and has securement means extensions therefrom so that when brought together into a closed position about a body part, flap portions 6 and 7 may or may not meet each other, but the securement means extension thereof do meet each other in a way that allows for the securement means to mate to each other and secure the device in place without attaching to the central portion 8.

Figure 11:
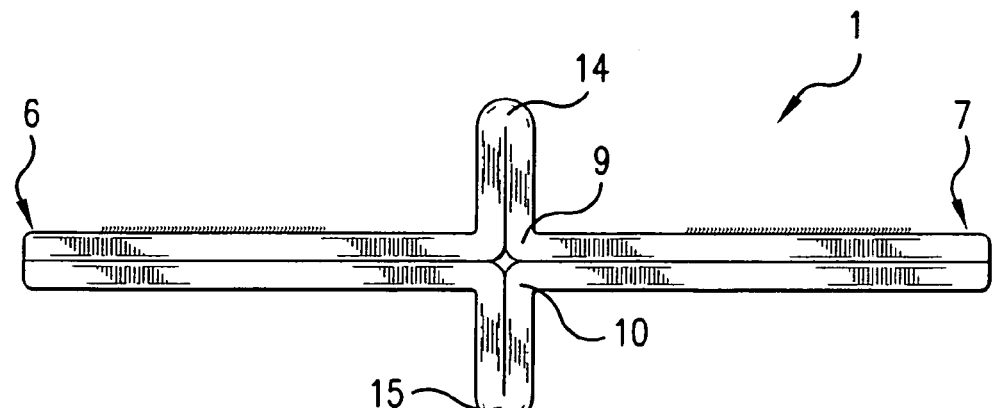
FIG. 11 is a front planar view of a device of 7 in a first alternate pre-use folded position.
Figure 12:
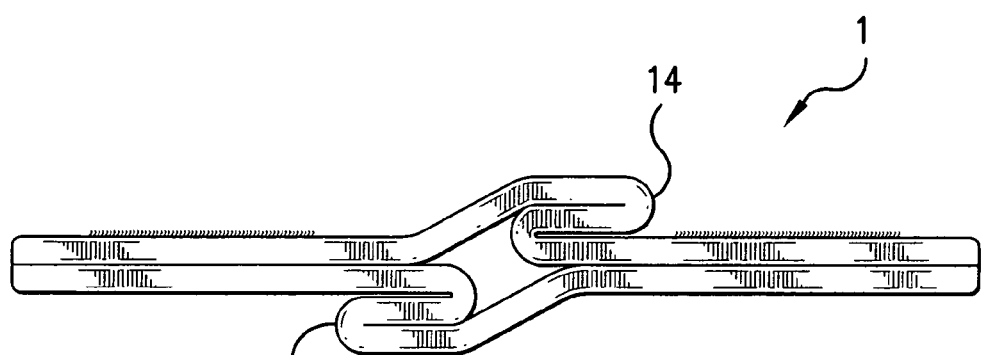
FIG. 12 is a front planar view of a device of 7 in a second alternate pre-use folded position.
Figure 13:
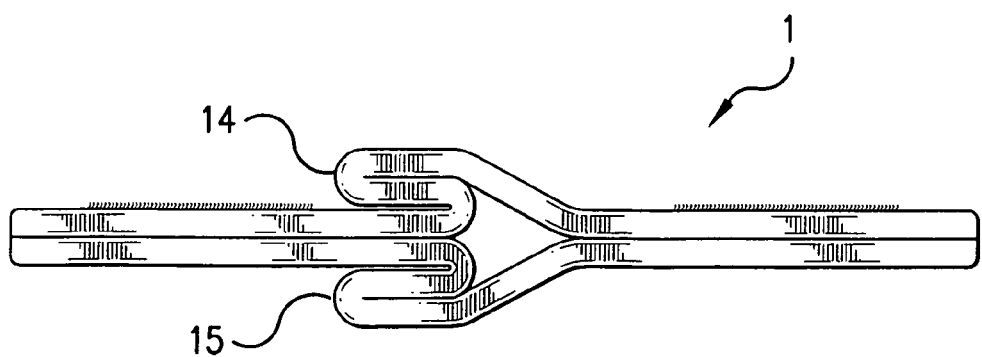
FIG. 13 is a front planar view of a device of 7 in a third alternate pre-use folded position.

FIGS. 11-13 show the device of FIG. 7 in which the device is in alternate pre-use folded positions rather than the flat opened position of FIGS. 6 and 7. In FIGS. 11-13, the peripheral ends of the flaps 6 and 7 (distal from the central portion 8) have been displaced centrally, but instead of opening the sleeve portion as in FIG. 8, the central portion 8 has not been opened, resulting in an upper minor flap 14 and a lower minor flap 15. FIGS. 12 and 13 show the device of FIG. 11 where the minor flaps have been displaced to opposite sides (FIG. 12) or to the same side (FIG. 13). For FIGS. 12 and 13, left and right may be interchanged without departing from the present invention. When positions such as those in FIGS. 12 and 13 are utilized, one must be sure that the securement means chosen is one which would not result in attachment between either of the flaps 6 and 7 on the one hand and flaps 14 and 15 on the other. Other alternate pre-use folded positions will be apparent to those of ordinary skill in the art without departing from the present invention. As an alternative, a securement means cover (not shown) which is not adherent to the other portions of the device in which it comes in contact may be used to prevent adherence of the securement means to other layers during manufacture, packaging, and storing of the device until such time as one is ready to apply the device. Suitable materials include any material which is easily removed when desired from the securement means and yet prevents adherence between the securement means and the rest of the device when in place. For example, when the securement means is Velcro, the securement means cover may be a piece of mated Velcro or a non-Velcro sleeve slipped over the securement means. Alternatively, where the securement means is an adhesive, the securement means is a releasable liner that can be easily removed from such adhesive. Where the securement means is a snap, no securement means cover is needed. It should be noted that securement means covers are not required and merely optional, but may, in fact, be preferred.

Figure 14A:
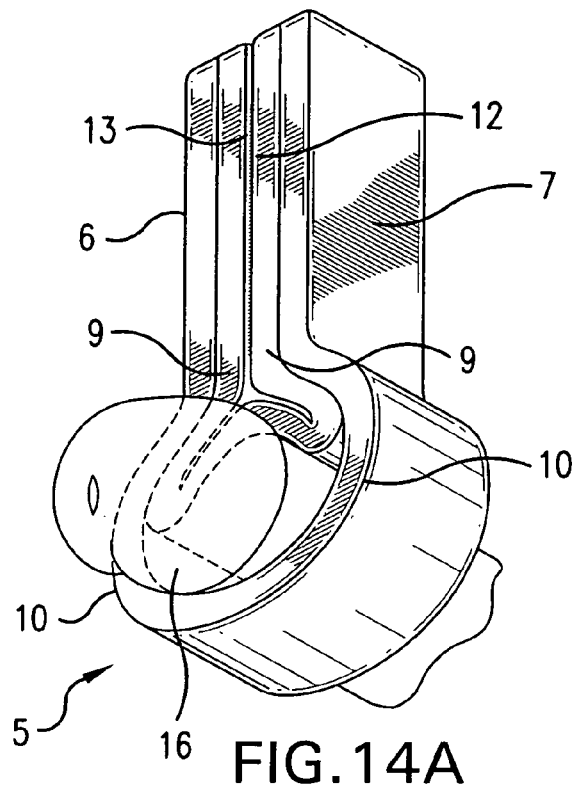
FIGS. 14 A and B are perspective views of an invention device applied in the context of a penile dressing.
Figure 14B:
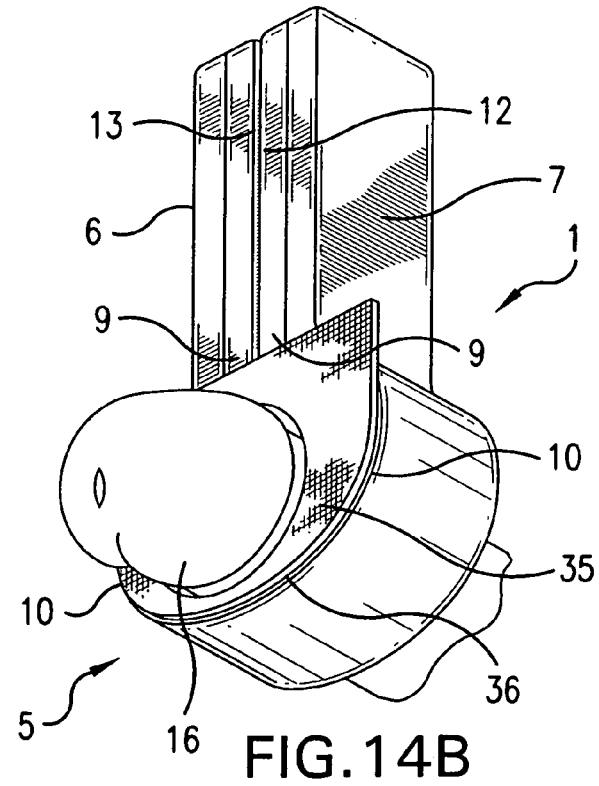

FIGS. 14 A and B show an embodiment of the present invention as applied and secured to a wounded penis 16 (such as after circumcision). As shown, the device has been applied to the penis, and right and left flaps 6 and 7 pulled together so as to allow securing means 12 and 13 to mate and secure the device. FIG. 14B shows the same arrangement as FIG. 14A except that a drainage member 35 (preferably a mesh fabric material) is also present, which is affixed to portion 10 in any suitable manner, such as by stitching 36. The orientation and shape of drainage member 35 is not critical and many other variations will be appreciated by those of ordinary skill. While drainage member 35 helps to isolate the circumcised penis, it is merely optional in the present invention.

Figure 15A:
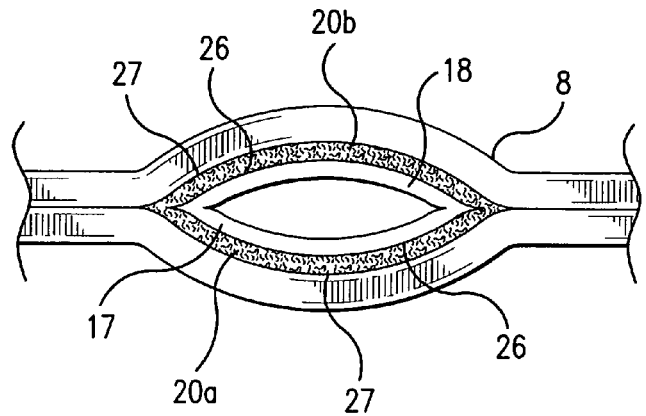
Figure 15B:
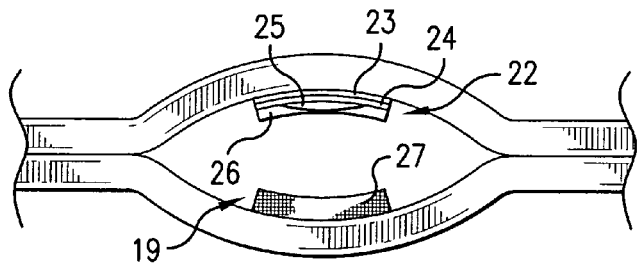
FIG. 15B shows a device of the invention wherein the active agent is contained within transdermal portions adhered to at least a portion of the skin contacting surface.
Figure 16:
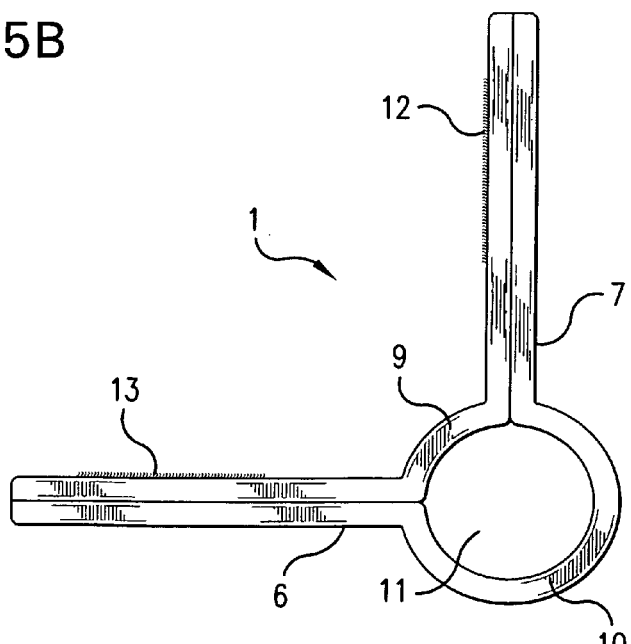
FIG. 16 shows an alternate embodiment of the present invention in an open position ready for use.
Figure 17:
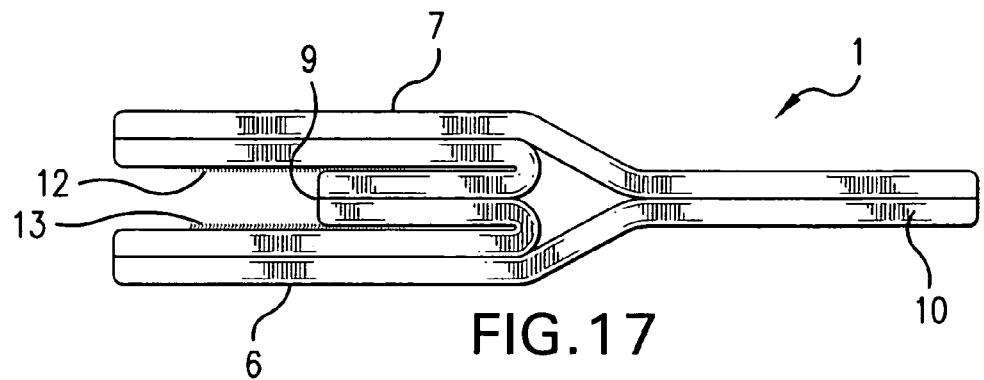
FIG. 17 shows the embodiment of FIG. 16 in a pre-use first folded position.
Figure 18:
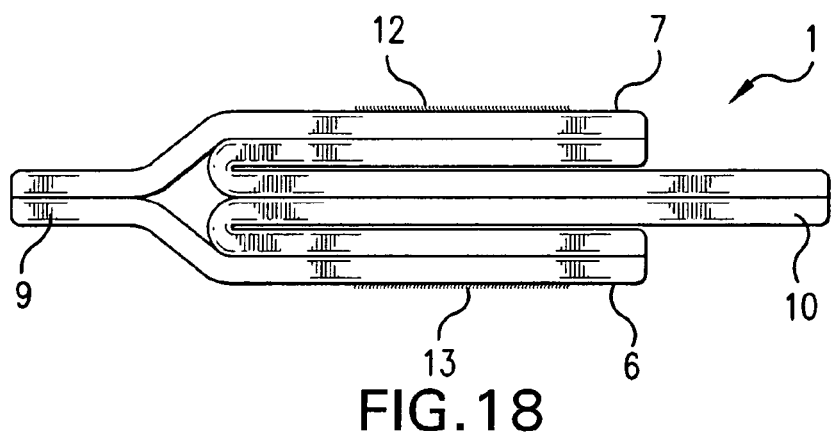
FIG. 18 shows the embodiment of FIG. 16 is a pre-use second folded position.
Figure 19:
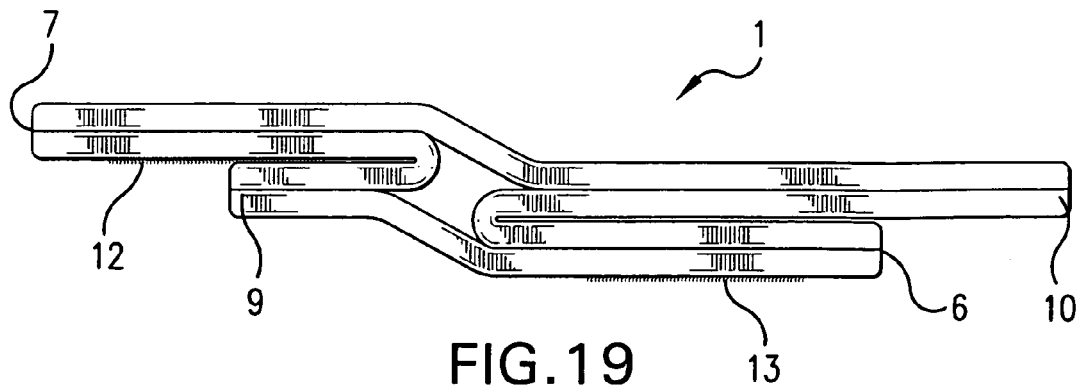
FIG. 19 shows the embodiment of FIG. 16 in a pre-use third folded position.

FIG. 15A is an enlarged view of central portion 8 of FIG. 8, showing the details of the protecting surfaces of the bandage portion which will impact against the body part or plant part to which the invention dressing is being applied. Generally, the center portion 8 includes an outer wall 27 formed by the outside surfaces of portions 20A and 20B and an inner wall 26 formed by the inner portions of opposing portions of 20A and 20B. Portions 20A and 20B may be gauze or any other suitable material. Lining portions 17 and 18 can be fitted flushly against the inner wall 26 and sandwiched between opposing portions 20A and 20B. While FIG. 15 shows portions 20A and 20B as only in the central portion 8, alternative and preferred embodiments have portions 20A and 20B extending partially into or completely across the left and right flap regions 6 and 7. In many embodiments, lining portions 17 and 18 are merely a coating which prevents adhesion or sticking of the device to the skin, such as petrolatum, which can be applied in the manufacturing process or can be added by the user at the time of use. Additionally, portion 20A and lining portion 17 may constitute a unitary layer if the material of portion 20A is naturally skin-non-adherent or is impregnated with a materials so as to be skin non-adherent. Xeroform® (petrolatum impregnated gauze with 3% bismuth tribromophenate) is one such suitable material (although the bismuth tribromophenate should preferably not be used with infants). Similarly, portion 20B and lining portion 18 may also constitute a unitary layer in the same fashion. The inner surface of central portion 8 (i.e., the lining portions 17 and 18 if present, or the portions 20A and 20B if lining portions 17 and 18 are not separately present), may additionally be impregnated with suitable active agents or formulations thereof for any of a variety of uses. Lining portions 17 and 18 or portions thereof, alone or together with corresponding segments of portions 20A and 20B may be transdermal formulations or transdermal devices that have been adhered to wall 27 (if lining portions 17 and 18 and portion 20A and 20B are otherwise not separately present in the respective area) or adhered to wall 26 (if lining portions 17 and 18 are not present but portions 20A and 20B are present in the corresponding area). One variant of this is shown in FIG. 15B, where two different transdermal regions are present using two different types of transdermal delivery. Use of transdermal delivery with the present invention can utilize a single transdermal delivery over all or a portion of the skin-contacting surface or as shown in FIG. 15 utilize different transdermal delivery portions that are the same or different from one another in the same device. In FIG. 15B, one portion of surface 27 carries a monolithic drug delivery portion 19 having one or more active agents dispersed in a non-skin-adhesive polymeric material, which may be cast directly on surface 27 (or onto surface 26 if portion 20A is present) or precast and fastened onto surface 27 (or onto surface 26) using a suitable adhesive. A second drug delivery portion 22 of the "reservoir pouch type" which generally comprises a drug-non-permeable (usually occlusive) backing 24, a drug permeable overlayer 26, backing 24 and overlayer 26 defining reservoir area 25 therebetween in which a liquid or semisolid drug formulation is contained, and an adhesive for adhering the backing layer to surface 27 (or to surface 26 if it is present). Generally, drug delivery portion 22 will be premanufactured and adhered to the appropriate layer of the invention device in the course of manufacture. However, where desired, premanufacture is not required and the drug delivery portions 19 and 22 can be integrated in the overall device manufacture process. In either case, where permeable drug delivery devices 19 and/or 22 are utilized additional barrier layers to prevent migration of the drug before use may be desirable (such as removable drug-non-permeable release liners, and barrier backings where the surface 27 or 26 is drug permeable) and those of ordinary skill will be well aware appropriate materials and placement thereof. Alternatively, premanufactured drug delivery devices 19 and 22 may be adhered with appropriate adhesives to surface 27 or 26 of the devices of the present invention at the time that the device is about to be applied to a particular body part. This allows for extensive variation in the type of drug to be applied as the particular case may call for. Drug delivery devices 19 and 22 may be designed for either merely topical delivery of drug or transdermal delivery, either locally or systemically as the case may be, without departing from the present invention. Other variations will be apparent to those of ordinary skill.

With respect to the active agents, reference to a free acid or base is intended to include reference to salts, esters, and amides thereof and vice versa, while reference to a compound that contains asymmetric centers is intended to include each of the individual optical isomers thereof and mixtures of optical isomers and reference to an individual optical isomer is intended to include reference to other optical isomers of the compound mentioned and mixtures therewith.

Most frequently, such active agents will include (but none is absolutely required), without limitation, (a) Anti-infectives such as, without limitation,
(i) topical anti-infectives (such as, without limitation, aminocrine, benzethonium chloride, bithionolate salts, bromchlorenone, cetalkonium halide, chlorhexidine, clioquinol, domiphen halide, fentichlor, fludazonium, furazolidone, gentian violet, halquinols, hexachlorophene, imedecyl iodine, iodine, mafenide acetate, meralein, methylbenzethonium chloride, nitrofurazone, nitrmersol, octenidine, oxychlorosene, povidone-iodine, silver nitrate, sulfadiazine, symclosene, thimerfonate, thimerosal, and troclosene);
(ii) antibacterials (such as without limitation, alamecin, alatrofloxacin, alexidine, amidinocillin, amicycline, amifloxacin, amikacin, amoxicillin, amphomycin, ampicillin, apalcillin, apramycin, aspartocin, asperlin, astromycin, avilamycin, avoparcin, azithromycin, azlocillin, bacampicillin, bacitracin, bambermycins, berythromycins, betamicin, biapenem, biniramycin, biphenamine, butikacin, butirosin, carbadox, carbenicillin, carumonam, cefaclor, cefadroxil, cefamandole, cefaparole, cefatirazine, cefazaflur, cefbuperazone, cefdinir, cefepime, cefetecol, cefixime, cefinenoxime, cefinetazole, cefonicid, cefoperazone, cefoxanide, cefotaxime, cefotetan, cefotiam, cefoxitin, cefpimizole, cefpiramide, cefpirome, cefpodoxime, cefprozil, cefroxadine, cefulodin, ceftazidime, ceftibuten, ceftizoxime, ceftriaxone, cefuroxime, cefacetrile, cephalexin, cephaloglycin, cephaloridine, cephalothin, cephapirin, cephadrine, cetocycline, cetophenicol, chloramphenicol, chlortetracycline, cinoxacin, cioprofloxacin, clarithromycin, clinafloxacin, clindamycin, cloxacillin, cloxyquin, colistimethate, coloistin, coumermycin, cyclacillin, dalfopristin, daptomycin, demeclocycline, demecycline, diaveridine, dicloxacillin, dihydrostreptomycin, dirithromycin, doxycycline, droxacin, enoxacin, eperezolid, epicillin, epitetracycline, erythromycin, fleroxacin, floxacillin, fludalanine, flumequine, fosfomycin, fumoxicillin, furozolium, fusidate, fusidic acid, gatifloxacin, gentmicin, gloximonam, gramicidin, grepafloxacin, haloprogin, hetacillin, hexedine, ibafloxacin, imipenem, josamycin, kanamycin, kitasamycin, levofloxacin, levopropylcillin, lexithromycin, lincomycin, linezolid, lomefloxacin, loracarbef, mafenide, meclocycline, megalomicin, mequidox, meprpenem, methacycline, methicillin, metioprim, mezlocillin, minocycline, mirinamycin, nafcillin, naldixic acid, nebramycin, neomycin, netilmicin, neutramycin, nifuradene, nifuraldezone, nifuratrone, nifurdazil, nifurimide, nifurpirinol, nifurquinazole, nifurthiazole, nitrocycline, norfloxacin, novobiocin, ofloxacin, ormetoprim, oxacillin, oximonam, oxolinic acid, oxytetracycline, paldimycin, paulomycin, pefloxacin, penamecillin, penicillin G, penicillin V, pentizidone, piperacillin, pirbenicillin, pirlimycin, pivampicillin, polymixin, propikacin, quindecamine, quinupristine, racephenicol, ramoplanin, ranimycin, relomycin, repromicin, rifametane, rifamexil, rifamide, rifampin, rifapentine, rifaximin, rolitetracycline, rosaramicin, rosoxacin, roxarsone, roxithromycin, sancycline, sanfetrinem, sarmoxicillin, sarpicillin, sisomicin, sparfloxacin, spectinomycin, spiramycin, stallimycin, streptinocozid, sulfabenzamide, sulfacetamide, sulfacytine, sulfadiazine, sulfadoxime, sulfalene, sulfamerazine, sulfameter, sulfamethiazine, sulfamethiazole, sulfamethoxazole, sulfamonothoxine, sulfamoxole, sulfanilate, sulfasalszine, sulfasomizole, sulfathiazole, sulfazamet, sulfisoxazole, sulfomyxin, sulopenem, sultamicillin, suncillin, talampicillin, teicoplanin, temocillin, tetracycline, tetroxoprim, thiamphenicol, thiphencillin, ticarcillin, tiodonium, tobramycin, tosufloxacin, trimethoprim, trisulfapyrimidines, troleandomycin, trospectmycin, trovafloxacin, tyrothricin, vancomycin, zorbamycin or mixtures thereof; preferably bacitracin, neomycin, polymixin or mixtures thereof);
  (iii) antifungals such as, without limitation, acrisorcin, ambruticin, amphotericin B, azaconazole, azaserine, basifungin, bifonazole, butenafine, butoconazole, candicidin, carbolfuchsin, chlordantoin, ciclopirox, cilofungin, cisconazole, clotrimazole, denofingin, dipyrithione, doconazole, econazole, enilconazole, ethonam, fenticonazole, filipin, fluconazole, flucytosine, fungimycin, griseofulvin, hamycin, isoconazole, itraconazole, kalafingin, ketoconazole, lomofungin, lydimycin, mepartricin, metacresol, miconazoile, naftifine, nifuratel, nifuramerone, nitralamine, nystatin, octanoic acid, omoconazole, orconazole, oxiconazole, oxifungin, parconazole, pyrrolnitrin, rutamycin, sanguinarium, saperconazole, scopafungin, sinefungin, sulconazole, terbinafine, terconazole, thiram, ticlatone, tioconazole, tolciclate, tolindate, tolnaftate, triacetin, triafungin, undecenylate, zinoconazole, and mixtures thereof);
  (iv) and mixtures thereof, broad spectrum anti-infectives being preferable over others;

(b) Local anesthetics (which may also be incorporated as desired to ease pain which main be present) include, without limitation, benoxinate, benzocaine, bupivocaine, butamben, chloroprocaine, cocaine, diamocaine, dibucaine, dyclonine, ethyl chloride, etidocaine, euprocin, isobutamben, lidocaine, mepevicaine, oxethazine, pramoxine, prilocaine, pyrrrocaine, risocaine, rodocaine, tetracaine, and mixtures thereof; preferably benzocaine, lidocaine, tetracaine, and mixtures thereof);

(c) Clotting agents and clotting aids (when bandaging wounds and clotting is desired), which may include, without limitation,
  (i) physical agents that create barriers to blood flow such as petrolatum, gelatin film, KY Jelly;
  (ii) thickening agents which upon dissolution in serum, increase its viscosity so as to slow blood flow from the wound;
  (iii) agents which activate, supplement, or replace a component of the normally fully developed innate clotting cascade mechanism; and mixtures thereof;
  and include, without limitation, antihemophilic factor, poliglusam, oxidized cellulose, thrombin, aminocaproic acid, ethamsylate, Factor II, Factor V, Factor VIIa, Factor VIII (recombinant forms available as Bioclate, Helixate FS, Kogenate FS, Recombinate and ReFacto), Factor IX (recombinant form available as BeneFix), Factor X, Factor XI, Factor XIa, Factor XII, Factor XIIa, Factor XIII, Factor XIIIa, prothrombin, vitamin K, gelatin film, oxsamarin, sulmarin, tranexamic acid, arachidonic acid, thromboxane$A_2$, inositol triphosphate, fibrinogen, high molecular weight kininogen, prekallihrein, tissue factor, calcium, topical and local vasoconstrictors (such as, without limitation epinephrine) and mixtures thereof.

In contexts where open wounds are not at issue, but bandages are used for either topical or transdermal administration of compounds, the active agents that can be present can be virtually any active agent that is useful topically or transdermally. In addition, active agents which could not be previously administered transdermally because the drug transport was insufficiently high enough to deliver therapeutic levels can now frequently be used transdermally because larger areas of the body can be employed because the skin-contacting adhesive usually employed in transdermal products can be avoided. Thus, the type of active agent that can be employed in this context with the present invention is virtually unlimited. In transdermal administration of active agents in this context, reservoir type transdermals, standard monolith type transdermals (where the monolith is an adhesive formulation) and monolithic transdermals where the monolith is non-skin-adhesive are all suitable. The present invention is particularly advantageous with non-skin-contacting-adhesive transdermals and reservoir type transdermals precisely because the skin contacting adhesive can be avoided.

In the particular embodiment used for circumcision wound healing in infants or pre-mature infants, clotting may not take place as efficiently as would in older children or adults. Thus, impregnating the central region 8 of device 1 with clotting Factors such as one or more of those set forth above, especially Factor VIII, Factor XII, and/or vitamin K or others known to be generally of use in promoting clotting helps to promote proper clotting and begin the healing process. Such bandages having clotting factors either impregnated therein or merely applied to the central portion skin contacting surfaces are also of use in treating wounds of known hemophiliacs. In such embodiments, the invention devices are significant improvements over the art in that while allowing for rapid local administration of various clotting factors, the bandages can be readily removed and changed without disturbing the clot so formed. Other patient populations for which such embodiments are particularly advantageous include diabetics, those with compromised immune systems (such as transplant patients, dialysis patients, those having radiation therapy or chemotherapy, radiation poisoning patients, and those presenting with HIV positive infection), and those with arthritis. The more rapid closing of the wound in these embodiments helps to protect against infection (extremely important for poor healers such as diabetics and immunocompromised patients and for use in settings where antibiotic resistant infectious organisms are likely present) and the design of the securement means as not being attached along the circumference, but rather protruding radially is of considerable benefit to those having arthritis in the hands or in the body part being bandaged.

The skin contacting surface of the central portion 8 can be replaced in whole or in part by a transdermal device which can be adhered to the innermost wall within central portion 8 by a suitable adhesive, or the transdermal formulation can be merely impregnated into the portions 20A, 20B, or linings 17 and 18. Since the devices of the present invention can cover significant areas of the body because they do not use skin contacting adhesives, they can be used to administer active agents with lesser amounts of permeation enhancers than other transdermal devices known in the art, preferably substantially without penetration enhancers, most preferably without any. Furthermore, since the area of transdermal delivery can be large, the administration of drugs that are poorly administrable transdermally are possible to a greater degree, and the rate of permeation can be much lower so that prolonged transdermal administration of low flux is feasible. Unlike other transdermal devices known in the art, the present invention permits for lesser skin irritation due to less use of skin contacting adhesives and lesser use of skin permeation enhancers, yet the securement means maintains bandage/skin contact over large areas. Prior art "reservoir type" transdermal devices having adhesive only on the periphery of the device, did use lesser amounts of adhesive than monolithic type devices, but they suffered from the disadvantage that over large areas, the devices would not maintain optimal skin contact especially where body movement would create ripples in the skin. Even further, the larger areas that are now potentially able to be covered, would have been unacceptable with the skin-contact-adhesive devices of the art simply because removing such devices would be difficult and painful due to the presence of hairs. Even further, in situations where the transdermal permeability is adequate with a particular drug or formulation, occlusive dressings of most prior art transdermals becomes less of a concern and one can move to a breathable type of transdermal. The greater area for transdermal administration allows for a less efficient rate of permeation as when non-occlusive dressings are employed. Nonetheless, where desired, one will not depart from the present invention if one wishes to use the present invention in the context of a transdermal administration using permeation enhancers, skin-contacting adhesives, and/or occlusive materials.

In use, the bandages of the present invention are unfolded from one of the pre-use folded positions, and central portion 8 opened for receiving a body or plant part. If starting from the positions shown in FIGS. 6 and 7, pressure is placed on flaps 6 and 7 centrally. Depending upon the resiliency of the particular materials of which the device 1 is made, such central pressure may naturally open sleeve portion 11 or top portion 8 and bottom portion 9 may require some assistance to open into the correct orientation. The body part or plant part to which the bandage is to be applied is slipped into the sleeve portion and the flaps 6 and 7 are brought together while initially applying a slight amount of pressure on the top portion 9 of central portion 8 near the juncture of flaps 6 and 7 with central portion 8 allowing attachment means 12 and 13 to mate and secure the device in place. In a preferred embodiment, the body part to which the device is applied is an injured penis, more preferably a recently circumcised penis, most preferably a recently circumcised infant penis.

The preferred securement means is Velcro, but any securement means will be suitable. The fact that the securement means is not circumferentially attached about the body part means that in removing the bandage, the securement means can be undone without applying forces to the body or plant part being treated so as to reduce discomfort to the patient and have less of an undesired impact on the healing process while changing bandages than bandages which are secured circumferentially.

Figure 20:
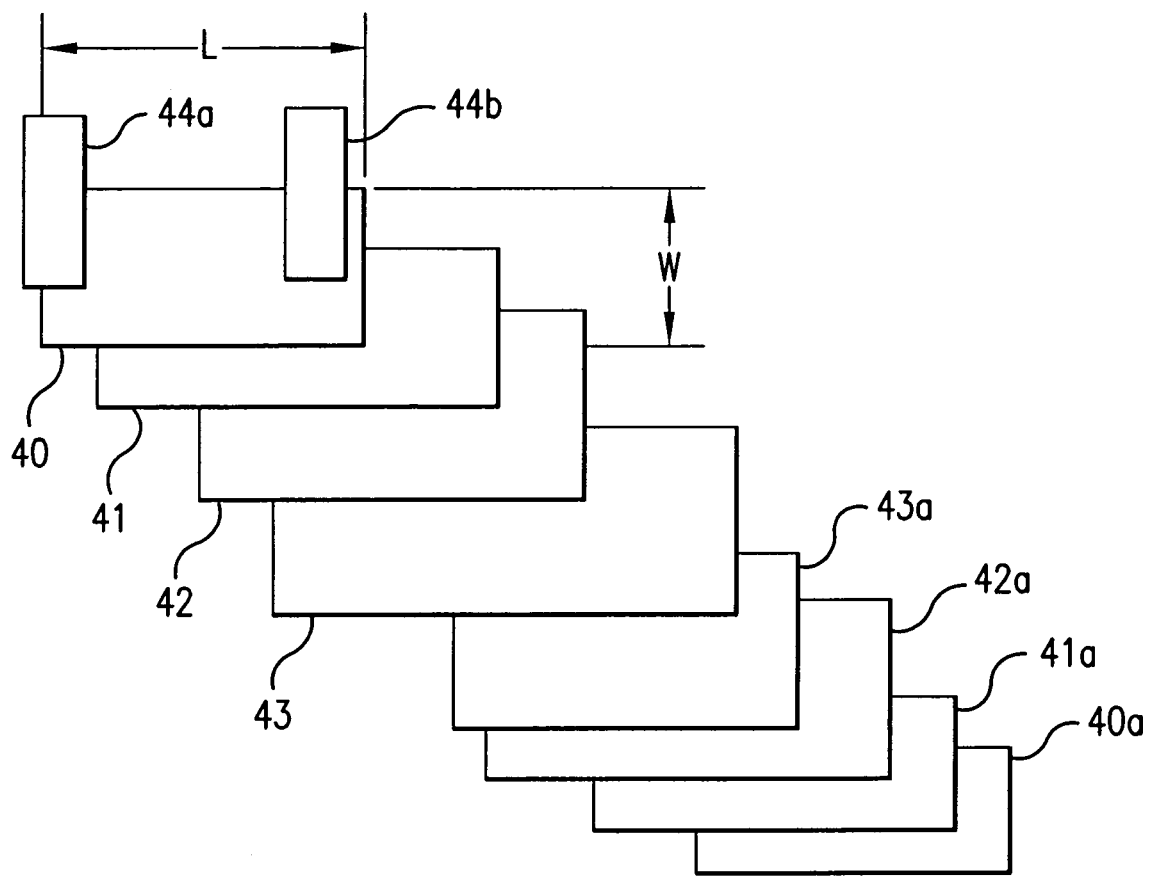
FIG. 20 shows an exploded view of another embodiment of the present invention.

In a further embodiment of the invention, one or more of the layers described above may actually be a multilaminate itself. A general exploded view of one embodiment of this type is shown in FIG. 20 where the device is laid out flat with layers 40-43 constituting a top portion (inclusive of securement means 44a and 44b) and layers 40a-43b constituting a bottom portion. Layers 43 and 43a are a skin-non-adherent layer and will be the skin contacting surface of the present invention. Layers 42 and 42a are an absorbent layer. Layers 41 and 41a are a waterproof material, and layers 40 and 40a are a decorative layer. Of these, the critical layer to have present is the non-adherent skin contacting layer or a coating of a skin non-adherent material that can be placed on the otherwise skin adherent material at any time prior to use so as to assure that the bandage is not skin-adherent. The only other important portion is the securement means and its placement outside of the central portion of the completed device so that the securement means from opposite portions of the device can be brought together in the manner described earlier. Securement means 44a and 44b may span across the entire width W or only a portion thereof, but preferably extends across the entire width W. In addition, one or both of securement means 44a and 44b need not be completely within the dimension L, but may optionally extend from within L to outside of L. Nonetheless, in preferred embodiments each of layers 41-43, 41a-43a and securement means 44a and 44b are all present. In a most preferred embodiment, layers 40 and 40a are also present.

Skin-non-adherent layers 43 and 43a (when no skin-non-adherent materials are added post manufacture) are typically comprised of non-adherent polyethylene or polypropylene apertured film, with the polyethylene film being preferred since the polypropylene material is more rigid. One such non-adherent polyethylene apertured film exemplary of the class is DelStar Delnet® polyethylene apertured film which is advantageously used in a thickness of about 1 to about 10 mils thick, preferably about 2 to about 8 mils thick, more preferably about 4 to about 6 mils thick. Other apertured films of other wound skin non-adherent materials are also possible and will be known to those of ordinary skill in the art. In addition, otherwise wound adherent materials may be utilized if they are suitable covered in the wound or skin contacting area with an ointment layer such as those made using a petrolatum base. Layers 43 and 43a may be coated with an ointment if desired (and is so if the fabric used is not a wound non-adherent material), and such ointment may contain active agents such as without limitation, antiseptics, anti-infectives, topical anesthetics, aids to clotting, and other wound healing materials. Alternatively, and especially when the layers 43 and 43a are inherently wound non-adherent, and therefore no ointment type covering in the skin contact layer is used, the layers 43 and 43a may be impregnated or have layered thereon one or more active agents such as without limitation, antiseptics, anti-infectives, topical anesthetics, aids to clotting, and other wound healing materials. In an alternative embodiment, layers 43 and 43a may be eliminated when the layers 42 and 42a are either themselves non-wound adherent or if layers 42 and 42a carry an ointment as described above to serve the wound non-adherent function.

Absorbent layers 42 and 42a are typically, but not required to be non-woven polyester pads and are present for the purpose of absorption of blood (in the case of human or animal wound dressings or of plant wound exudates in the case of plants wound dressings. One suitable alternative is polypropylene, but this is less advantageous because the polyester is the better absorber so that thinner layers could be used and it is economically more desirable as it is cheaper, has a nice bright white color for esthetic purposes, and it sterilizes well. One such polyester is DelStar non-woven polyester pad. The thickness of this layer will vary depending upon the absorption capacity of the exact material chosen and the absorption capacity thereof. Bandages for small wounds where less blood and exudates is anticipated will be able to be adequately addressed with relatively thinner layers, while those for larger wounds or for wounds where larger volumes of blood or exudates are anticipated will be better served with thicker layers and more absorbent layers 42 and 42a. Super absorbent materials that may also serve as alternatives for these layers include those absorbent materials utilized in disposable diapers, disposable undergarments, and sanitary napkins, which are well known in the art.

Waterproof layers 41 and 41a, while not absolutely required, are highly desirable. This is a thin flexible barrier layer to prevent leakage of blood or exudates out of the bandage, and when used in the context of an infant circumcision bandage aids in keeping urine from wetting the wound area. A typical exemplary waterproof material is a polyurethane film of about 0.5 to about 4 mils thick, preferably about 1 to about 2 mils thick. Other waterproof layer materials that can be suitably used include those used to line disposable diapers, disposable undergarments, and sanitary napkins. Occlusive barrier layers known in the transdermal drug delivery art are also suitable and may be used where desired for the waterproof layers 41 and 41a if so desired.

Decorative layers 40 and 40a are not required for the functioning of the device of the present invention but are generally present to provide both an overall aesthetic soft touch and to allow for printed matter such as an aesthetic design, instruction, or branding information. Spun laced fabric formed by hydroentanglement (used in a wide range of products such as hospital gowns, drapes, and bandages) is particularly suitable. Exemplary commercial materials include, without limitation, Dupont Sontara® or Dupont Softesse®. Again, outer layer printable soft materials utilized in commercially available disposable diapers, undergarments, and sanitary napkins are suitable alternatives if desired.

Securement means 44a and 44b are generally selected from hook and loop materials (usually known as Velcro), adhesives, snaps, and other generally known means of securing two materials together, hook and loop fasteners or adhesives being preferred, with loop and hook fasteners being most preferred. A highly preferred embodiment has Velcro as the securement means with one of 44a and 44b being the loop portion and the other being the hook portion.

In a most preferred embodiment, other than the securement means, the completed device is symmetric about the center line in terms of layers present, that is each of layers 40-43 that are present in the top portion has a corresponding layer 40a-43a representing the bottom portion and arranged in the same sequence as viewed from the center going toward the top and the center going toward the bottom. Nonetheless, there is no requirement that such symmetry be present for in all embodiments. In an exemplary manner of constructing the device of the invention, a symmetric embodiment will be employed, but the invention includes other manners of constructing the device whether or not such symmetry is present.

While the securement means 44a and 44b are shown in the figures at the left and right ends of flap portions 6 and 7 and cover the entire width of the flap (as viewed from front to back), the securement means is not required to traverse the full width of the flap portion, but preferably does. Thus, a securement means 44a or 44b may be for example only across a portion of the width of the flap and may be placed centrally (as viewed front to back) or off center either closer to the front or closer to the back (each as viewed from front to back) provided that the portions 44a and 44b are each placed in the same type of arrangement so that the portions 44a and 44b can mate when the bandage is in use. Additionally, flaps 6 and 7 are shown in the figures as being of the same length as viewed from central portion 8 towards the portion distal thereto either to the right or left. However, central portion 8 need not be at the center with two equal sized flaps extending therefrom. An arrangement where one of flaps 6 and 7 extends longer from central portion 8 than the other of flaps 6 and 7 is still within the scope of the present invention, as long as when flaps 6 and 7 are brought together, securement portions 44a and 44b can mate to effectively secure the bandage in place. Nonetheless, it is generally preferable to have flaps 6 and 7 extend for equal distances from central portion 8.

For an example of a manufacture of a bandage according to the invention, the following utilizes the embodiment having soft touch material layers 40 and 40a, waterproof layers 41 and 41a, absorbent layers 42 and 42a, wound non-adherent layers 41 and 41a, and Velcro securement means portions 44a and 44b. Individual rolls of the soft touch material, waterproof material, absorbent pad material, and wound non-adherent material are layered together in sequence and combined into a composite roll using heat seal, and/or pressure seal, and/or ultrasonic sealing techniques known in the art. Adhesive sealing can also be used alone or in conjunction with any of the above but the use of adhesives between the absorbent layer and the wound non-adhesive layer would either require the adhesive being present only on the periphery or in some sort of pattern print to permit adequate permeation of fluids to the absorbent layer unless the adhesive is sufficiently permeable not to materially interfere with the function of the absorbent layer. Suitable adhesives and selective adhesive layer printing on a roll of material, as well as adhesives that are compatible with heat sealing, pressure sealing, and/or ultrasonic sealing techniques are well known in the transdermal art and one of ordinary skill can utilize any such materials and techniques in the manufacture of the present invention. Nonetheless, because of the selectivity of adhesives and the more expensive manufacturing techniques of selective printing of adhesives, it is preferable not to use adhesives between the absorbent layer and the wound non-adherent layer. The composites so formed may be (1) cut into appropriate width ribbons, the ribbons combined as below, and then cut into appropriate lengths or (2) the composites so formed may be combined as set forth below and then the combined intermediate cut into appropriate width ribbons, which are then cut into appropriate lengths. Either way, the composite (in this example having layers 40, 41, 42, and 43 along with any adhesive that may have been used, and having identical layer in reverse order, i.e., 43a, 42a, 41a, and 40a) are brought together with layer 43 facing layer 43a. Optional non-adherent ointment (with or without active agents) or an active agent solution may be applied to layers 43 and 43a either before they are brought-together (and the operation may require a temporary release liner being utilized to roll the composite having such ointment or active solution applied thereto) or during the operation of combining the two composite rolls. The two rolls are adhered to each other via heat sealing and/or pressure sealing and/or ultrasonic sealing and/or adhesive sealing techniques known in the art such that central region 8 is not sealed, but the regions that will become flap portions 6 and 7 are sealed to each other. The result of this sealing operation then has the securement means 44a and 44b applied to one of layers 40 and 40a in the appropriate regions, which may be sealed thereto in any of the sealing manners mentioned above, namely, heat sealing and/or pressure sealing and/or ultrasonic sealing and/or adhesive sealing techniques. The end result is the cut in known manners (for example, without limitation as by die cutting or chopping) to the appropriately sized finished bandage.

I claim:

1. A wound dressing comprising an upper and lower layer, defining therebetween, a central tubular portion and spaced apart flaps, said tubular portion having an inner surface which is designed to receive a body part therein; and said upper layer having a top surface distal from said inner surface and said lower layer having a bottom surface distal to said inner surface and distal to said top surface; and securement means on the top surface of said spaced apart flaps, such that when said top surfaces of said spaced apart flaps are brought together, said securement means on the respective flaps mate with each other and secure said dressing in place so that the act of dressing the wound or removing the dressing is accomplished without said flaps being circumferentially adhered to said tubular portion and further wherein said dressing does not have skin-contacting adhesives.

2. The wound dressing of claim 1 further comprising one or more active agents.

3. The wound dressing of claim 2 wherein said active agents are selected from the group consisting of blood cloning factors, local anesthetics, and antisepsis agents.

4. The wound dressing of claim 1 wherein said body part or plant part is a substantially cylindrical portion of the body.

5. The wound dressing of claim 4 wherein said body part is selected form a digit, a limb, the neck, the body trunk, a breast, and a penis.

6. The wound dressing of claim 5 wherein said body part is a penis.

7. The wound dressing of claim 1 wherein said dressing comprises from said inner surface outwards toward either said top surface or said bottom surface, a skin-non-adherent layer, an absorbent layer, and a waterproof layer.

8. The wound dressing of claim 7 wherein said wound dressing further comprises a decorative layer external to said waterproof layer.

9. The wound dressing of claim 1 wherein said securement means is selected from the group consisting of hook and loop fasteners, adhesives, snaps, self-adhesive material, and adhesive.

10. A wound dressing comprising an upper and lower layer, defining therebetween, a central tubular portion and spaced apart flaps, said tubular portion having an inner surface which is designed to receive a body part therein; and said upper layer having a top surface distal from said inner surface and said lower layer having a bottom surface distal to said inner surface and distal to said top surface; and securement means on the top surface of said spaced apart flaps, such that when said top surfaces of said spaced apart flaps are brought together, said securement means on the respective flaps mate with each other and secure said dressing in place without adhering to said central tubular portion so that the wound is dressed without die application of pressure by the dressing around or against the body part that would cut off blood flow to portions of the body part distal to the dressing once the dressing is applied, and further wherein said dressing does not have skin-contacting adhesives.

11. The dressing of claim 1 wherein said dressing can be removed without involving said body part in the act of opening the dressing for removal thereof.

12. The dressing of claim 10 wherein said dressing can be removed without involving said body part in the act of opening the dressing for removal thereof.

13. The dressing of claim 2 wherein said active agent is present in a topical or transdermal presentation, each without the use of a skin-contacting adhesive.

14. The wound dressing of claim 10 further comprising one or more active agents.

15. The wound dressing of claim 14 wherein said active agent is present in a topical or transdermal presentation, each without the use of a skin-contacting adhesive.

16. A method of administering an active agent to the skin of a substantially cylindrical body part from a dressing designed to accommodate said body part therein without the use of a skin-contacting adhesive to adhere said dressing comprising applying said active agent to or incorporating said active agent within said dressing of claim 1 and applying said dressing along with said active agent thereon or therein to said body part.

17. A method of administering an active agent to the skin of a substantially cylindrical body part from a dressing designed to accommodate said body part therein without the use of a skin-contacting adhesive to adhere said dressing comprising applying said active agent to or incorporating said active agent within said dressing of claim 10 and applying said dressing along with said active agent thereon or therein to said body part.

* * * * *